United States Patent
Meganck et al.

(10) Patent No.: US 10,667,693 B1
(45) Date of Patent: Jun. 2, 2020

(54) SYSTEMS, METHODS, AND APPARATUS FOR INTERFERENCE FILTER CORRECTION BASED ON ANGLE OF INCIDENCE

(71) Applicant: PerkinElmer Health Sciences, Inc., Waltham, MA (US)

(72) Inventors: Jeffrey Meganck, Grafton, MA (US); Joshua Kempner, Medway, MA (US); Matthew Royal, Medford, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 16/193,236

(22) Filed: Nov. 16, 2018

(51) Int. Cl.
  *G01N 21/64* (2006.01)
  *A61B 5/00* (2006.01)
  *G01N 21/76* (2006.01)

(52) U.S. Cl.
  CPC ....... *A61B 5/0071* (2013.01); *G01N 21/6456* (2013.01); *G01N 21/763* (2013.01); *A61B 2503/40* (2013.01); *A61B 2562/0233* (2013.01); *A61B 2576/00* (2013.01); *G01N 2021/6471* (2013.01); *G01N 2201/063* (2013.01)

(58) Field of Classification Search
  CPC ............. G01N 21/6456; G01N 21/763; G01N 2021/6471; G01N 2201/063
  See application file for complete search history.

(56) References Cited

U.S. PATENT DOCUMENTS

| | | | | |
|---|---|---|---|---|
| 5,446,510 A | * | 8/1995 | Mitsutake | G02B 27/283 348/E9.027 |
| 6,167,202 A | * | 12/2000 | Fukui | G03B 7/16 396/157 |
| 6,404,499 B1 | * | 6/2002 | Stoeldraijer | G03F 7/70066 250/492.22 |
| 7,030,958 B2 | * | 4/2006 | Luijkx | G03F 7/70066 355/30 |
| 7,231,243 B2 | * | 6/2007 | Tearney | A61B 1/00082 600/407 |
| 7,537,732 B2 | * | 5/2009 | Gustafson | G01N 1/38 356/318 |
| 8,237,786 B2 | * | 8/2012 | Danuser | G01N 21/636 348/79 |
| 8,908,151 B2 | * | 12/2014 | Muramatsu | G02B 3/06 355/53 |

(Continued)

OTHER PUBLICATIONS

Mar. 27, 2019—(WO) International Search Report and Written Opinion—App PCT/US2018/061741.

*Primary Examiner* — David P Porta
*Assistant Examiner* — Djura Malevic
(74) *Attorney, Agent, or Firm* — Banner & Witcoff, Ltd.

(57) ABSTRACT

Aspects of the present disclosure provide systems, methods, devices, and computer-readable media for interference filter correction based on angle of incidence. In some examples, a sample emits an emission spectrum that is filtered by an emission filter to provide a transmission spectrum. The emission spectrum illuminates the emission filter at multiple angles of incidence. The angles of incidence result in a spectral shifting of the transmission spectrum. Based on this spectral shifting, the intensity of the transmission spectrum is corrected. An image corresponding to the corrected intensity of the transmission spectrum may be generated.

19 Claims, 9 Drawing Sheets
(6 of 9 Drawing Sheet(s) Filed in Color)

(56) References Cited

U.S. PATENT DOCUMENTS

| | | | | |
|---|---|---|---|---|
| 9,172,848 B2* | 10/2015 | Imoto | ............ | H04N 1/6027 |
| 10,249,035 B2* | 4/2019 | Sundvor | ............ | G06T 7/001 |
| 2002/0094131 A1* | 7/2002 | Shirakawa | ............ | H04N 5/2176 |
| | | | | 382/274 |
| 2003/0139886 A1* | 7/2003 | Bodzin | ............ | G01N 21/47 |
| | | | | 702/28 |
| 2005/0140957 A1* | 6/2005 | Luijkx | ............ | G03F 7/70066 |
| | | | | 355/71 |
| 2007/0136017 A1* | 6/2007 | Wang | ............ | G06K 9/00496 |
| | | | | 702/85 |
| 2007/0141567 A1* | 6/2007 | Wulfman | ............ | C12Q 1/6837 |
| | | | | 435/6.11 |
| 2008/0137080 A1* | 6/2008 | Bodzin | ............ | G01N 21/47 |
| | | | | 356/300 |
| 2009/0052019 A1* | 2/2009 | Brueck | ............ | G02B 21/18 |
| | | | | 359/370 |
| 2009/0278954 A1* | 11/2009 | Kanamori | ............ | H04N 9/045 |
| | | | | 348/222.1 |
| 2013/0050546 A1* | 2/2013 | Kano | ............ | H04N 5/3572 |
| | | | | 348/280 |
| 2014/0153801 A1* | 6/2014 | Sarkozy | ............ | G16B 20/00 |
| | | | | 382/129 |
| 2016/0363749 A1* | 12/2016 | Yamashita | ............ | G02B 21/008 |
| 2017/0124690 A1* | 5/2017 | Sundvor | ............ | G06T 7/001 |

* cited by examiner

*AOI: angle of incidence*

US 10,667,693 B1

SYSTEMS, METHODS, AND APPARATUS FOR INTERFERENCE FILTER CORRECTION BASED ON ANGLE OF INCIDENCE

TECHNICAL FIELD

The disclosures herein relate generally to imaging systems and methods. More particularly, in some examples, the disclosure relates to an interference filter correction based on angle of incidence.

BACKGROUND

High throughput imaging, e.g., in vivo imaging, has been an attractive field of research due to its applications in biology and medicine. High throughput imaging may involve the images of one or more live subjects at a time (e.g., mice), and may involve a large field of view. As a result, high throughput imaging may inherently lead to angular dispersion of light. For example, there may be a variation in the angle of incidence of light striking the emission filter as it reflects from the sample. Unfortunately, this variation may affect the final intensity of the transmission spectrum. For example, an increase in the angle of incidence may lead to a shift in the wavelength of light allowed to pass through the emission filter. As this may affect the accuracy of the imaging of the sample, and may adversely influence the observations and conclusions drawn from the imaging, there is thus a desire and need to correct transmission spectra based on the angle of incidence. Furthermore, it may be burdensome, time-intensive, ineffective, and impractical for users to have to correct a transmission spectrum manually, without involving the mechanisms leading to the raw data itself.

Various implementations of the present disclosure address one or more of the challenges described above. For example, the present disclosure may describe systems, methods, devices, and apparatuses for interference filter correction based on angle of incidence.

SUMMARY

Aspects of the disclosure relate to techniques for interference filter correction based on the angles of incidence at which an emission spectrum illuminates an emission filter thereby causing spectral shift in the transmission spectrum from the emission filter.

The disclosure provides, for example, a method for generating an image. A transmission spectrum may be received from an emission filter. The transmission spectrum may correspond to a selected wavelength range of an emission spectrum that is filtered by an emission filter. The emission spectrum may illuminate the emission filter at multiple angles of incidence, including those that deviate from a normal angle of incidence with respect to the emission filter. An intensity of the transmission spectrum may be measured and/or stored. Based on a spectral response of the emission filter as a function of the angles of incidence, a corrected intensity for the transmission spectrum may be obtained, and an image based on the transmission spectrum and the corrected intensity may be generated.

In certain examples, the emission spectrum may be emitted from a luminescent source in a sample, e.g., a fluorescent source. The luminescent source may be a luminescent reporter expressed within the sample by a luminescent cell line. The luminescent reporter may be exogenously administered. In one example, the luminescent reporter may be administered to the sample as a component of a probe. The sample may be biological (e.g., a live mouse).

The emission filter has a field of view over which it is illuminated by the emission spectrum. The locations of the emission filter's field of view may be characterized using, e.g., (x, y) position coordinates. For each position within the field of view, the emission spectrum may illuminate the emission filter at a respective angle of incidence. The angle of incidence may influence the measured intensity of the transmission spectrum from the emission filter at that position.

Each of the (x, y) coordinate positions of a field of view of the emission filter, over which the emission spectrum illuminates the emission filter, may have a corresponding angle of incidence. In some examples, a corrected intensity may be based on an integration of individual intensity values of the intensity of the transmission spectrum. Each individual intensity value may correspond to a respective (x, y) coordinate position and the corresponding angle of incidence for the respective (x, y) coordinate position.

The acquired image may be based on the measured intensity of the transmission spectrum and may be corrected for the angles of incidence of the emission spectrum on the emission filter's field of view. The acquired image may be a digital pixel-based image in which each pixel corresponds to a respective (x, y) coordinate position of a field of view of the emission filter, over which the emission filter receives the emission spectrum. The value of the pixel in the acquired image may correspond to the raw intensity of the transmission spectrum measured at the corresponding (x, y) coordinate position of the emission filter's field of view. The raw intensity of the transmission spectrum at a particular (x, y) coordinate position may correspond to the portion of the emission spectrum that illuminates that position of the emission filter at a particular angle of incidence.

To correct for the angles of incidence, a correction image may be determined. The correction image may include data to correct for the variations resulting from the different angles of incidence across the field of view of the emission filter. To obtain the correction information, a ratio between the integration of two convolutions may be determined. The first convolution may be a performed on a function characterizing a known intensity of a reporter (e.g., a fluorophore) and a function characterizing the transmission spectrum from the emission filter for a particular (x, y) coordinate position and its corresponding angle of incidence. The second convolution may be performed on the function characterizing the known intensity of the reporter and a function characterizing the transmission spectrum from the emission filter at the normal (i.e., orthogonal) angle of incidence. The results of these convolutions may be integrated between upper and lower wavelength cutoff thresholds (e.g., near the short, blue end of the spectrum and the long, red end of the spectrum). The ratio between the results of these integrations may provide the correction information used to correct the intensity of the transmission spectrum measured at the particular (x, y) coordinate position. Correction information for each (x, y) coordinate position of the emission filter may be obtained using this technique.

The correction information may be used to generate a correction image that may be applied to the raw image acquired by measuring the intensity of the transmission spectrum from the emission filter. For example, a final convolution of the acquired raw image and the correction image may be performed to obtain a corrected image. The corrected image may be a pixel-based image in which the value of each pixel corresponds to the intensity of the transmission section at a corresponding (x, y) coordinate position of the emission filter's field of view that has been corrected for the angle of incidence corresponding to that position. The corrected image may thus provide a more accurate representation of the emission spectrum from the sample as it accounts for the spectral shifting that occurs (due to the different angles of incidence) when the emission filters the emission spectrum to provide the transmission spectrum measured by the detector.

The disclosures below also provide an imaging device that may include, for example, a light source, one or more excitation filter(s), one or more emission filter(s), and a illumination detector, among other components. The light source may provide an excitation spectrum while the excitation filter(s) may provide, toward a sample being imaged, a selected excitation wavelength range from the excitation spectrum. The emission filter(s) may provide a transmission spectrum. The transmission spectrum may include a selected emission wavelength range of an emission spectrum received from the sample and filtered by the emission filter. The emission filter(s) may receive the emission spectrum at multiple angles of incidence that deviate from a normal angle of incidence with respect to the emission filter. The illumination detector may measure an intensity of the transmission spectrum. The detector may generate a signal corresponding to the transmission spectrum that is, in turn, used to generate a digital image of the reporter (e.g., a fluorophore) that may be in the sample and that emits at least a portion of the emission spectrum. In some examples, a specially-programmed computing device is configured to correct the intensity based on spectral shifting of the transmission spectrum as a function of the various angles of incidence. The device may or may not include collimating optics positioned between the sample and the emission filter. The correction information may represent a correction to each pixel of the acquired image.

The techniques described below may be used to generate, in particular, a fluorescence image. For example, fluorescence image data may be acquired, e.g., a raw, digital, pixel-based image corresponding to the measured intensity of a transmission spectrum provided by an emission filter by filtering an emission spectrum of a fluorophore. The techniques described herein may provide corrections to the pixels of the fluorescence image, and a corrected fluorescence image may be generated using that correction information.

The fluorophore and the emission filter may be selected by a user. Furthermore, the optical performance of the emission filter may be evaluated and additional corrections may be applied to generate the corrected image. These additional corrections may involve, e.g., correcting for optical distortion, vignetting, and read bias in the optical path.

It should be appreciated that aspects of the various examples described herein may be combined with and/or substituted for aspects of other examples (e.g., elements of claims depending from one independent claim may be used to further specify implementations of other independent claims). Other features and advantages of the disclosure will be apparent from the following figures, detailed description, and the claims.

The objects and features of the disclosure can be better understood with reference to the drawings described below, and the claims. In the drawings, like numerals are used to indicate like parts throughout the various views.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
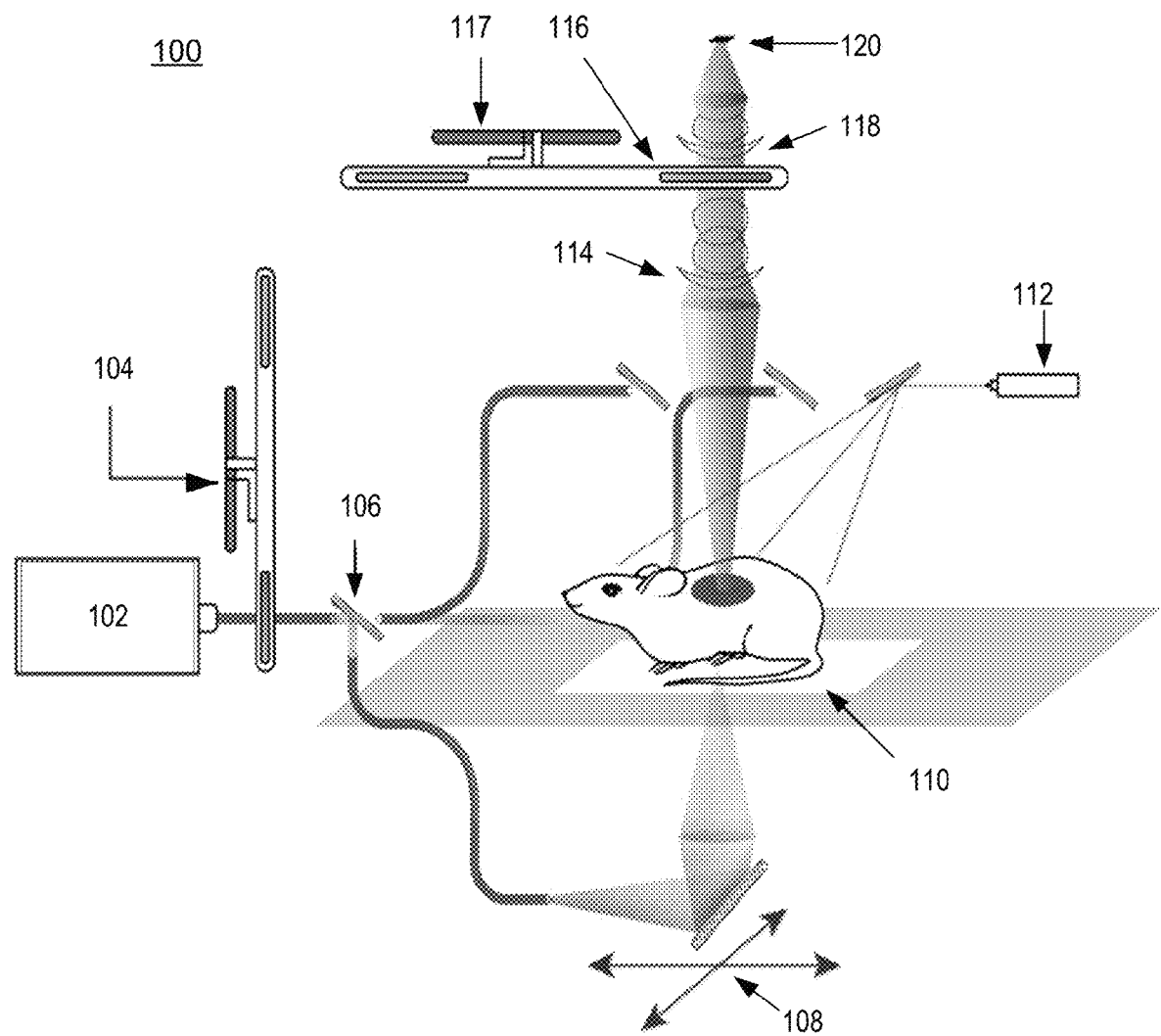
FIG. 1 is a diagram of an example of an optical imaging system.

It is contemplated that methods, systems, and processes described herein encompass variations and adaptations developed using information from the examples described herein.

Throughout the description, where systems and compositions are described as having, including, or comprising specific components, or where processes and methods are described as having, including, or comprising specific steps, it is contemplated that, additionally, there are systems and compositions of the present disclosure that consist essentially of, or consist of, the recited components, and that there are processes and methods of the present disclosure that consist essentially of, or consist of, the recited processing steps.

As used herein, the term "image" is understood to mean a visual display or any data representation that may be interpreted for visual display. For example, a two-dimensional image may include a dataset of values of a given quantity (e.g., pixels) that varies in two spatial dimensions.

Described herein are techniques for correcting for the angular dispersion resulting from the respective angles of incidence across the field of view of a filter used in an imaging system. Due to those angles of incidence, the transmission of the filter varies across filter's field of view. For example, at the edge of the filter's field of view, the light from the sample illuminates the filter at a higher angle of incidence than near the center of the field of view. The techniques described herein correct for these angles of incidence in order to provide a more accurate image of the light emitted by a subject during an imaging operation. For convenience, the illumination transmitted by the filter is referred to herein as a transmission spectrum. At least some examples of the techniques described herein generate an image based on a transmission spectrum with a corrected intensity. The corrected intensity may account for any wavelength shifts caused by a variation in the angle of incidence. The generated image may enhance the information obtained during an imaging procedure, e.g., the quantitative, structural, functional, and/or molecular information obtained during in in vivo imaging studies. This increase in accuracy may be realized by normalizing raw image data (e.g., pixel-by-pixel) to known, estimated, or simulated image data corresponding to a reference angle of incidence (e.g., an angle of incidence normal to the emission filter)

As described above, differing angles at which light is incident on an emission filter may cause spectral shifts in the transmission spectra. During emission spectroscopy, for example, such spectral shifts may result in a non-uniform fluorescent image. In emission spectroscopy, an emission filter may be used to accurately detect various fluorophores and other reporters (e.g., the tags that illuminate when certain genes, proteins, etc. are detected/excited by a light source). For example, in clinical settings, multiple samples (e.g., animals) may be imaged to increase throughput and reduce time (e.g., ten mice at once versus one mouse at a time). However, imaging multiple samples may involve a higher field of view, which may cause angular dispersion of light as it strikes the emission filter, which causes the spectral shifts affecting the data measurements. Thus, angular dispersion of light striking the emission filter may pose issues for imaging in clinical, research, and/or diagnostic contexts. The techniques described herein correct for those spectral differences.

In some examples, this disclosure further enables the use of analytical tools to rely on or customize the image obtained by the interference filter correction based on angle of incidence, resulting in improved accuracy. These tools may provide information related to, e.g., in vivo animal optical imaging setups through the image generated by the interference filter correction.

FIG. 1 is an example of an optical imaging system 100. The optical imaging system may include any imaging device involving a luminescent source and an emission filter where rays of illumination may potentially strike at an angle. It will be appreciated that the illumination emitted by the luminescent source may include both visible light and non-visible light (e.g., ultraviolet, infrared). The optical imaging may be used for in vivo imaging of the luminescent source. The optical imaging system 100 may be employed for various types of spectroscopy such as, for example, emission spectroscopy. The optical imaging system 100 may be employed to obtain measurements of the light emitted by the luminescent source. Such measurements may be employed, for example, to generate an image corresponding to the luminescent source. The luminescent source may be a substance or protein that emits light, e.g., as a result of a reaction.

The optical imaging system may be employed to measure (e.g., image) various types of luminescent sources. For example, the luminescent source may be a fluorescent source, a bioluminescent source, a phosphorescent source, a chemiluminescent source (e.g., one that emits light as a result of a chemical reaction, for example, a fluorescent source), an electrochemiluminescent source (e.g., one that emits light as a result of an electrochemical reaction), a lyoluminescent source (e.g., one that emits light as a result of dissolving in a solid in a liquid), a candoluminescent source (e.g., one that emits light when its temperature is elevated, e.g., when exposed to a flame), a crystalloluminescent source (e.g., one that emits light during crystallization), an electroluminescent source (e.g., one that emits light when an electric current is passed through), a mechanoluminescent source (e.g., one that emits light as a result of a mechanical action on a solid), a photoluminescent source (e.g., one that emits light as a result of absorption of photons, e.g., as in fluorescence), a radioluminescent source (e.g., one that emits light as a result of bombardment by ionizing radiation), a thermoluminescent source (e.g., one that emits light as a result of the re-emission of absorbed energy when a substance is heated), or a combination thereof. The sample may be biological. A biological sample may be live or deceased. In one example, if the sample is a live subject (e.g., a mouse), then a luminescent source may be incorporated in or on the subject (e.g., endogenous, ingested, injected, infused, topically applied, and the like). For example, luminescent source(s) may include fluorophores and other reporters that bind to biological structures (e.g., antibodies, membrane proteins, etc.) that emit fluorescence, e.g., that help reveal details about the biological structures. Additional examples will be appreciated with the benefit of the additional disclosures set forth herein.

The techniques described herein could be employed in a variety of imaging systems that use visible light.

The components of the example optical imaging system 100 are described below by way of example in the context of emission spectroscopy in which excitation light is used to excite luminescent sources (e.g., fluorophores) in a sample and in which emission light from the luminescent sources is measured. It should be appreciated, however, that other types of optical imaging systems may include additional and alternative components. The components of the example optical imaging system 100 are presented in the order that the light originates and passes through them in a typical operation, i.e., along the optical path. In this example, the optical imaging system 100 includes a light source 102, an excitation filter 104, a fiber bundle switch 106, a sample 110, a primary objective lens 114, an emission filter 116, a secondary focusing lens 118, and detector 120.

The light source 102 may be any be any device (e.g., a lamp) that generates light to provide illumination toward the sample. The light may be visible or invisible (e.g., ultraviolet, infrared, etc.) to the human eye. The illumination from the light source 102 is referred to herein as an excitation spectrum for convenience. For emission spectroscopy, the light source 102 may include a broadband lamp with a xenon (Xe) bulb. Similarly and also for convenience, the excited light emitted by the sample in response to the excitation spectrum is referred to herein as an emission spectrum.

The excitation filter 104 may be an optical device that filters light as it travels from the light source 102 toward the sample 110 so that a selected wavelength or wavelength range from the excitation spectrum reaches the sample 110. The optical imaging system 100 may provide multiple excitation filters to choose from, and the user may select which excitation filter to use.

A fiber bundle switch 106 may assist in diverting the light as it exits the excitation filter 104 towards various points of the sample 110, e.g., via fiber optic cable. In some implementations, a laser galvanometer 112 may be used to provide light to an internal structure and/or reveal surface topography of the sample 110. Furthermore, a stage 108 that can translate the excitation light focusing optics in two dimensions (e.g., the x and y dimensions) for the imaging of the sample.

The optical imaging system 100 may include collimating optics positioned between the sample 110 and the emission filter 116. In another example, the device 100 may omit collimating optics. Collimating optics may include one or more lenses that align the rays of the emission spectrum, e.g., before it reaches the emission filter 116.

The emission filter 116 may similarly be an optical device that filters light (e.g., the emission spectrum) as it travels from the sample 110 toward the detector 120 so that a selected wavelength or wavelength range reaches the detector. The light transmitted by the emission filter 116 (i.e., the light from the emission spectrum that is allowed to pass through the emission filter) is referred to herein as the transmission spectrum for convenience. As described above, the emission filter 116 may receive the emission spectrum at a plurality of angles of incidence that deviate from a normal (e.g., orthogonal) of reference angle of incidence with respect to the emission filter. The optical imaging system 100 may provide multiple emission filters to choose from, and the user may select which emission filter to use via a filter wheel 117. Based on the selected excitation and emission filter(s), the wavelength of the light may shift in a way that is dependent on the luminescent source (e.g., fluorescence reporter). However, as described herein, the angle at which the light strikes the emission filter 116, relative to a normal or reference angle of incidence with respect to the emission filter 116 may also affect the transmission spectrum.

The optical imaging system 100 may also include one or more objective lenses to focus the emission and transmission spectrums. For example, the optical imaging system 100 may include a primary objective lens 114 positioned between the sample 110 and the emission filter 116 to focus the emission spectrum. The optical imaging system 100 may also include a secondary focusing lens 118 positioned between the emission filter 116 and the detector 120 to focus the transmission spectrum. The lenses may be adjusted by the user.

The optical imaging system 100 may include a detector (e.g., fluorescence detector) that may measure an intensity of the transmission spectrum. The detector 120 may be a light-sensitive device that would transform the light received to image data. For example, detector 120 may be a charge coupled device (CCD) detector. A CCD detector, or other like detectors, may include various detector elements that may build up a charge based on the intensity of light. In some aspects of the present disclosure, other detectors of electromagnetic radiation may be used, e.g., photomultiplier tubes, photodiodes, and avalanche photodiodes, etc. The image data may be received by a computing device of the optical imaging system 100.

As will be described below with reference to FIG. 5, the optical imaging system 100 may include a computing device programmed for interference filter correction based on angle of incidence. For example, the computing device may be programmed to correct the measured intensity of the transmission spectrum based on spectral shifting of the transmission spectrum as a function of the various angles of incidence at which light strikes the emission filter 116.

Figure 2A:
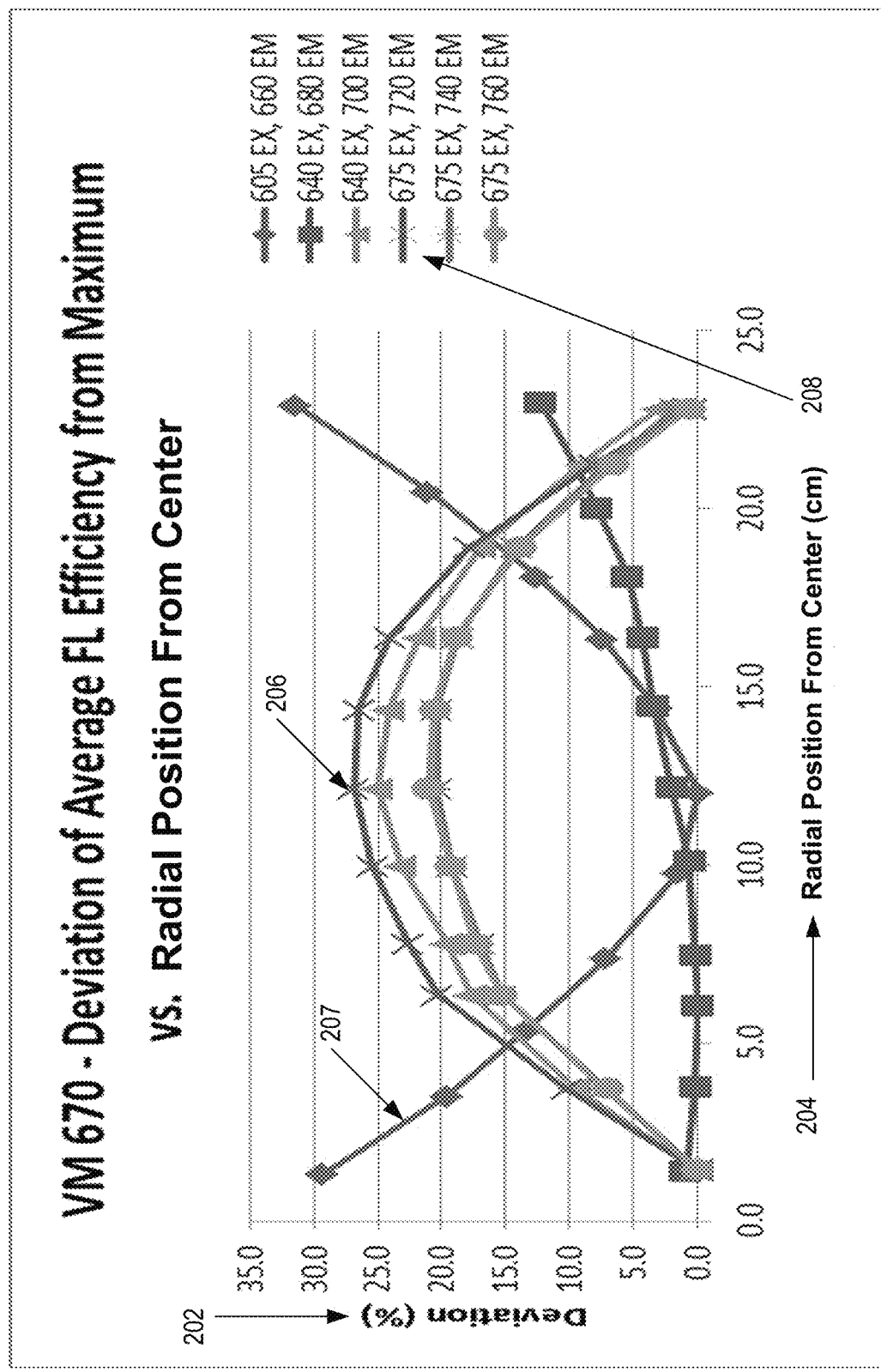
FIGS. 2A-2C are graphs depicting example measurements of transmission spectra resulting from the respective angles of incidence across the field of view of an emission filter.
Figure 2B:
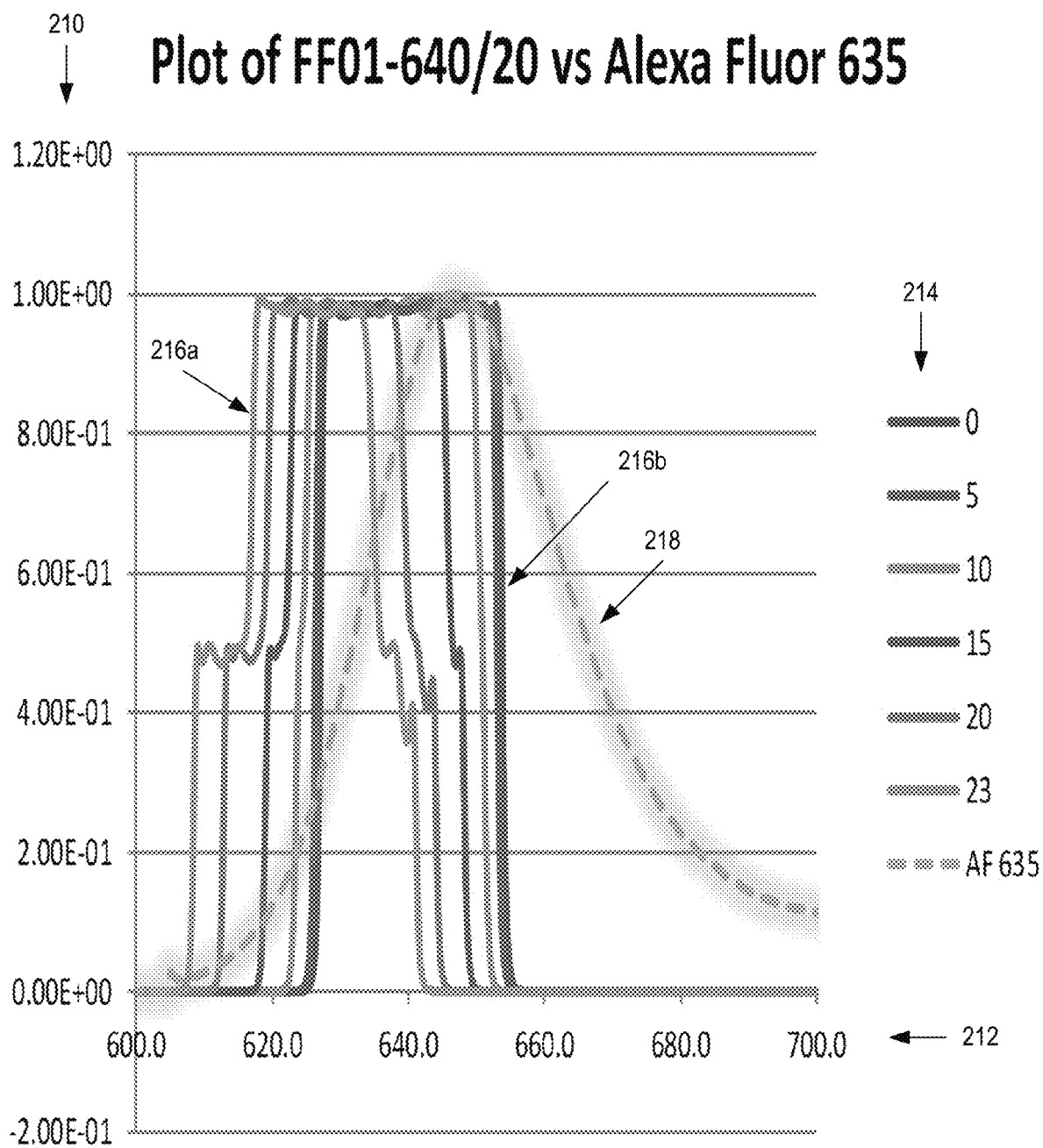
Figure 2C:
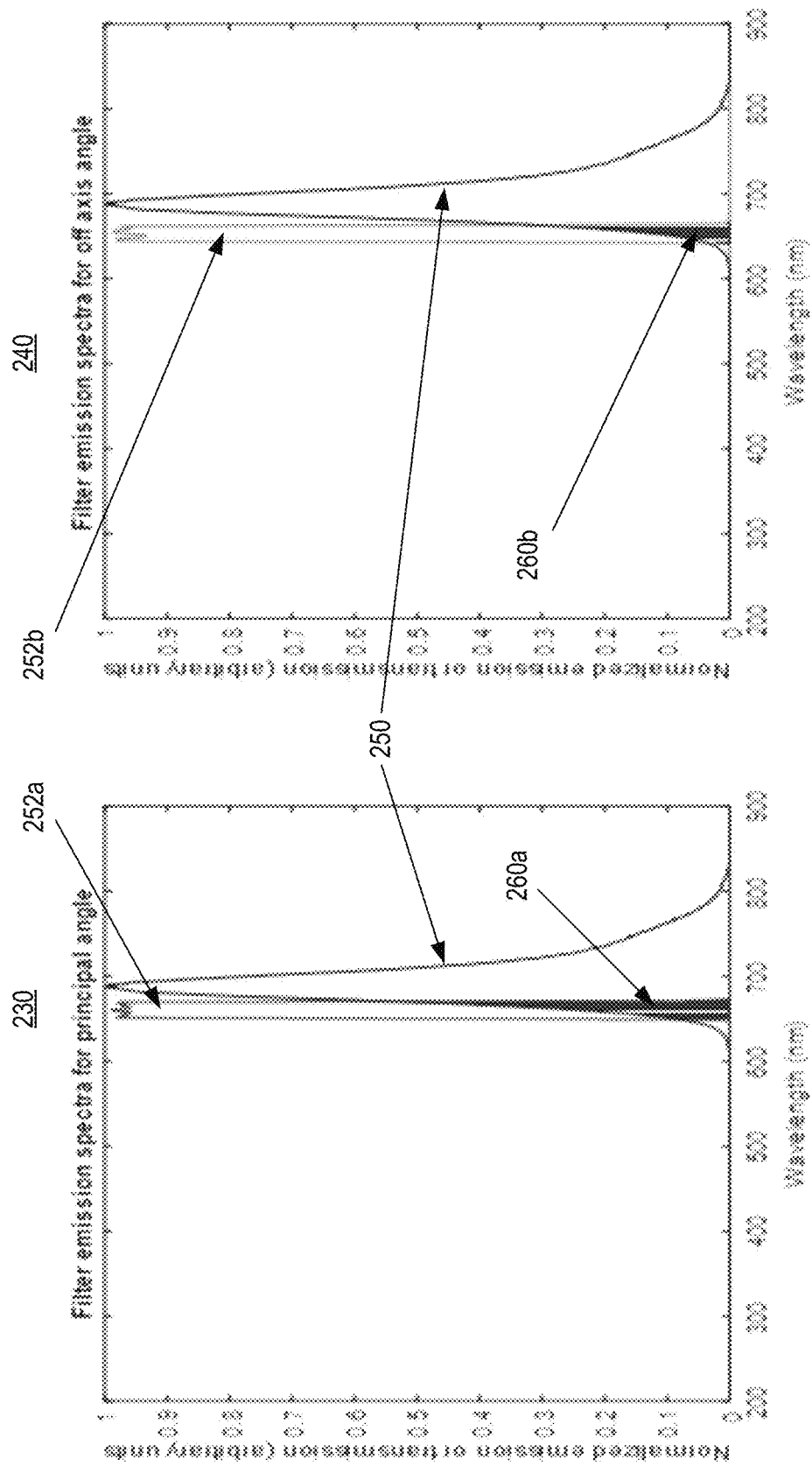

FIGS. 2A-2C illustrate graphs of example results depicting a variation of transmission spectra caused by variations in angles of incidence that have been observed for example wavelengths. As discussed above, variations in the angle of incidence by which light from a sample strikes an emission filter may cause shifts in the wavelength of light allowed to pass through the emission filter. These shifts may affect the measured intensity of the transmission spectrum. As this may affect the accuracy of the imaging of the sample 110, and may adversely influence the observations and conclusions drawn from the imaging, there is thus a desire and need to correct measurements of the transmission spectra based on the angle of incidence.

FIG. 2A depicts a graph plotting a percentage deviation in average fluorescence efficiency 202 from maximum fluorescence efficiency as a function of radial position 204 from the center of an emission filter's field of view for a variety of excitation and emission filters 208, e.g., an excitation (EX) filter at 605 nanometers (nm) and an emission (EM) filter at 660 nm. Fluorescence efficiency may be based on a ratio of the number of photons transmitted, e.g., from the emission filter, to the number of photons absorbed along the way from the light source, e.g., by the sample. The radial position may be expressed as a distance from the center, e.g., along a horizontal centerline from the center. Thus, the radial position 204 corresponds to a position along a horizontal centerline of the emission filter's field of view, where a position of zero may indicate the center of the emission filter's field of view. At the center of the emission filter's field of view, the angle of incidence may be perpendicular relative to the field of view, i.e., may correspond to the normal (orthogonal) angle of incidence. Positions of the emission filter's field of view located away from the center may correspond to angles of incidence that deviate from the normal angle of incidence with the most extreme angles of incidence corresponding to those positions located the farthest from the center of the emission filter's field of view. As seen in FIG. 2A, the radial position 204 correlates with the percentage deviation of fluorescence efficiency from the maximum fluorescence efficiency. The percentage deviation in average fluorescence efficiency 202 may indicate a variation in intensity of the transmission spectrum for a given position in the field of view. For example, a large deviation at a particular horizontal position may indicate a large increase or decrease in intensity of the transmission spectrum resulting from the particular angle of incidence of light striking the emission filter at that radial position (e.g., position from the center of the emission filter's field of view). The increase or decrease in intensity of the transmission spectrum may relate to where the filter curve is with respect to the peak wavelength of the optical reporter.

FIG. 2A shows that the percentage deviation of average fluorescence efficiency from the maximum is not uniform across excitation filters and emission filters. For example, the curve 206 corresponds to a 675 nm excitation filter and a 720 nm emission filter (i.e., a 675 EX, 720 EM filter pair). As seen in FIG. 2A, the 675 EX, 720 EM filter pair yields a peak deviation of about 27% at about 12 centimeters (cm) along the horizontal centerline and minimum deviation (e.g., about 0%) at about 2 cm and about 23 cm along the horizontal centerline. In contrast, the curve 207 corresponding to the 605 EX, 660 EM filter pair yields peak deviations of about 30% at about 2 cm and about 23 cm along the horizontal centerline and a minimum deviation (e.g., about 0%) at about 12 cm along the horizontal centerline.

FIG. 2B is a graph depicting the transmission percentages 210 of an example fluorophore (e.g., Alexa Fluor 635) and an example emission filter (e.g., a 640/20 nm single-band bandpass filter) across a wavelength range 212 (e.g., 600-700 nm). The solid curves 216 (collectively) represent the transmission percentages for the transmission spectra from the emission filter at various angles of incidence 214 (e.g., 0° to 23°) within the wavelength range 212. The dashed curve 218 represents the transmission percentages of the fluorophore's emission spectrum within the wavelength range 212. As seen in FIG. 2B, the transmission spectra from the emission filter shift significantly as the angle of incidence increases. For example, curve 216a corresponding the transmission spectrum for the most extreme angle of incidence in this example (e.g., 23°) has shifted leftward (e.g., to about 610-640 nm), which is a significant deviation from the curve 216b corresponding to the transmission spectrum (e.g., about 620-660 nm) at the normal angle of incidence (0°) for the 640/20 nm filter used in this example. This leftward shift towards shorter wavelengths as the angle of incidence increases may be referred to as blueshift. As also seen in FIG. 2, this blueshift causes the curve 218 corresponding to the emission spectrum of the fluorophore to overlap with less and less of the curves 216 corresponding to the transmission spectra of the emission filter. In other words, the emission spectrum of the fluorophore overlaps with more of the curve 216b at a smaller angle of incidence (e.g., 0°) and less of the curve 216a at a larger angle of incidence (e.g., 23°). This effect is illustrated in FIG. 2C.

FIG. 2C depicts a graph 230 of the transmission spectra for an emission filter at a reference (e.g., normal) angle of incidence and a graph 240 of the transmission spectra for the emission filter at an off-axis angle of incidence (i.e., an angle of incidence that deviates from the reference angle of incidence). Each graph includes a curve 250 corresponding to the emission spectrum of a fluorophore (i.e., a fluorophore emission curve), which stays constant in both graphs. Each graph also includes respective curves 252a and 252b corresponding to the measured transmission spectra from the emission filter at the reference and off-axis angles of incidence (i.e., a reference angle transmission curve and an off-axis angle transmission curve). As indicated by the shaded region 260a in graph 230, the reference angle transmission curve 252a overlaps the fluorophore emission curve 250. The off-axis angle transmission curve 252b similarly overlaps the fluorophore emission curve 250 as indicated by shaded region 260b in graph 240. In effect, the shaded regions 260a and 260b represent the respective integrals of the overlapping regions of the fluorophore curve 250 and the transmission curves 252a and 252b. The area of the two shaded regions 260a and 260b, however, differs: the shaded region 260a for the reference angle of incidence is larger than the shaded region 260b for the off-axis angle of incidence. This difference in the shaded regions 260a and 260b is a result of the shifting transmission spectra from the emission filter as the angles of incidence deviate from the reference (e.g., normal) angle of incidence. In other words, this difference can be explained by the different amounts of light from the emission spectrum transmitted by the emission filter at different angles of incidence. The emission filter transmits relatively more light near the center of its field of view (i.e., near the normal angle of incidence) and relatively less light near the edge of its field of view where the angle of incidence is more extreme. As a result, the respective integrals of the overlapping regions (e.g., shaded regions 260a and 260b) change due to the shift in the transmission spectra from the emission filter. In turn, the respective convolutions of the fluorophore curve 250 with the transmission curves 252a and 252b will also change as the angle of incidence changes. In other words, the integral of the convolution of the fluorophore curve with the measured transmission spectrum from the emission filter correlates with the angle of incidence of the emission spectrum on the emission filter.

The present disclosure provides techniques to correct for these shifts in the wavelengths of the transmission spectrum from the emission filter as a result of the deviations of the angles of incidence of the emission spectrum within the field of view of the emission filter. These techniques normalize the relatively fainter amount of light received at the emission filter at more extreme angles of incidence to the amount of light received at the center of the emission filter's field of view. Such techniques may provide normalizing values to apply to the measured transmission spectrum from the emission filter. Such normalizing values may correct for the differences in intensity resulting from angles of incidence that are closer to or farther from the normal angle of incidence at the center of the emission filter. Accordingly, such normalizing values may also be referred to as correction values.

In some examples, a two-dimensional pixel-based image may be generated that corresponds to the measured transmission spectrum from the emission filter. Each pixel in this acquired image may correspond to an intensity of the transmission spectrum at the corresponding location of the emission filter's field of view. In order to correct for the differences in intensity resulting from the different angles of incidence, a correction image may be generated. The correction image may include correction values that normalize the measured intensities across the emission filter's field of view to an intensity value (e.g., "1") corresponding to the center of the emission filter's field of view. In other words, the correction image may provide correction values that indicate the intensity of the measured transmission spectrum at respective angles of incidence relative to the intensity of the transmission spectrum at the center of the emission filter's field of view. This technique of using a correction image will be described in further detail below.

Figure 3A:
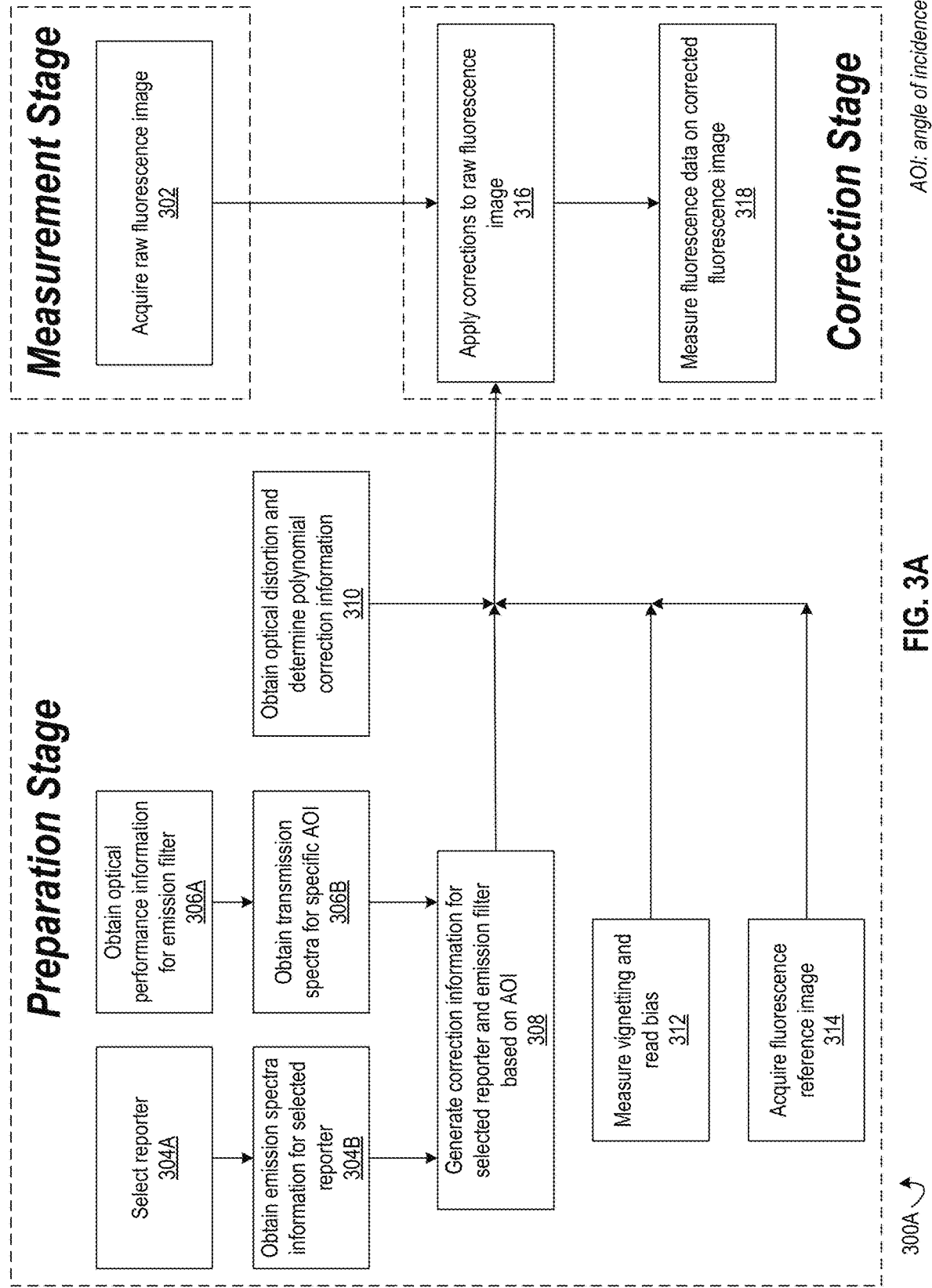
FIGS. 3A-3B depict example method steps for correcting for the angles of incidence on the field of view of an emission filter.
Figure 3B:
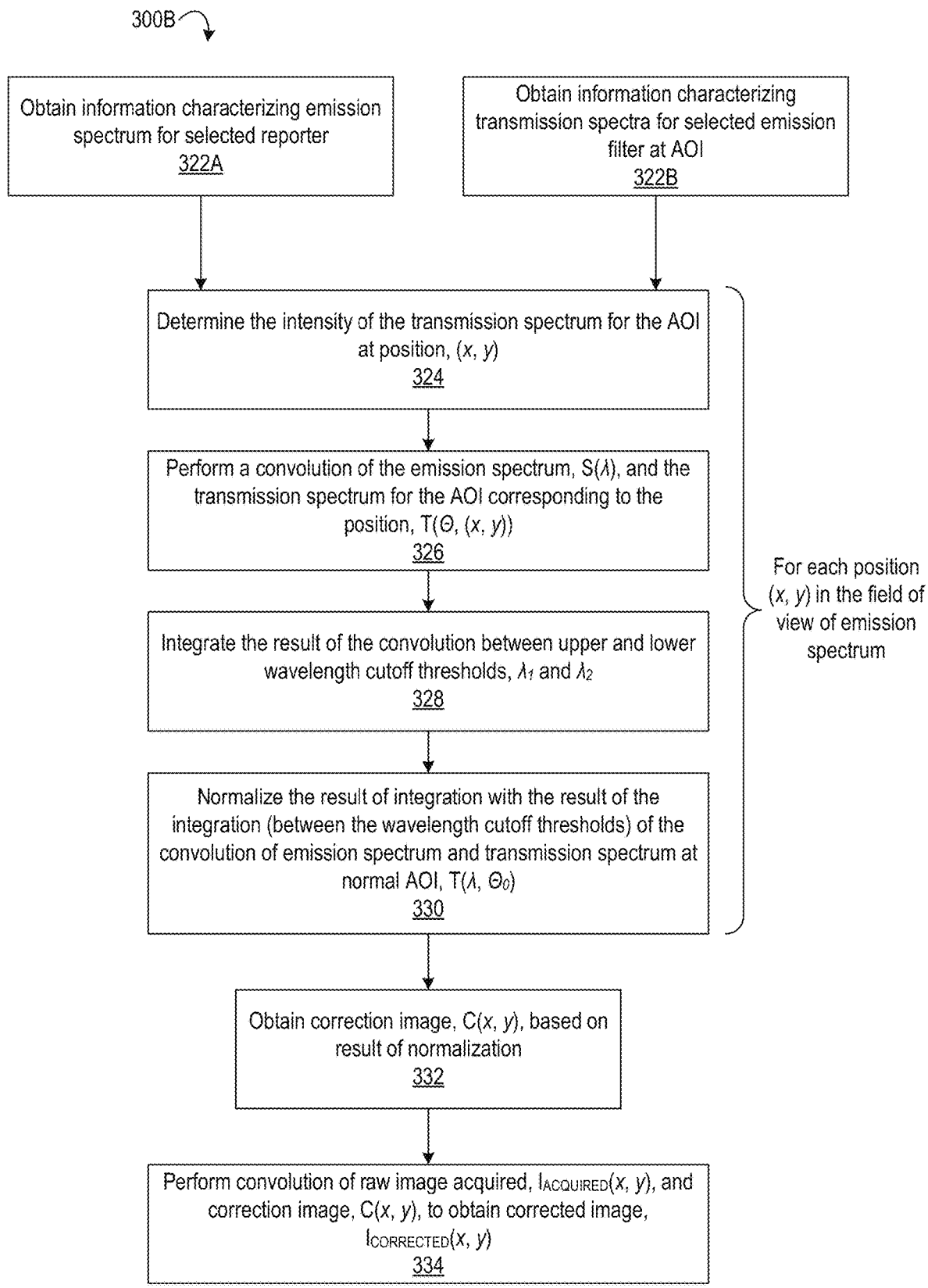

FIGS. 3A-3B are flowcharts 300A and 300B, respectively, of example method steps for interference filter correction. In some examples, methods 300A and 300B may be performed by a computing system or device ("computing device") of the optical imaging system. This computing device could be located locally or remotely (e.g., on a remotely-located server accessible via a network) relative to other components of the optical imaging system.

For example, FIG. 3A describes a method 300 of interference filter correction for an acquired image that generates, and enables measurement from, a corrected image. One or more steps of the method 300B, as depicted in FIG. 3B, may be performed by a specially-programmed computing device using one or more processors (e.g., computing device 500 in FIG. 5). While the steps described herein are example steps that may be performed for emission spectroscopy, additional or alternative steps may be performed for other types of optical imaging processes. For convenience, the method 300 can be understood as having three stages: a preparation stage, a measurement stage, and a correction stage. The preparation stage may generally be used to gather information needed to apply corrections during the correction stage to the raw image obtained during the measurement stage. Thus, at the preparation stage, a raw fluorescence image may acquired (step 302). The raw image may be produced by the optical imaging system using the components described above. For example, (1) a light source may illuminate a sample with an excitation spectrum, (2) the reporters (e.g., fluorophores) in the sample may be excited when illuminated by the excitation spectrum and emit an emission spectrum, (3) the emission spectrum may be filtered by the emission filter, and (4) a detector (e.g., a CCD) may detect the transmission spectrum transmitted by the emission filter to generate the raw fluorescence image. As noted above, focusing and collimating optics may be used to focus and align the emission spectrum and transmission spectrum on the emission filter and detector, respectively. Furthermore, as noted above, the emission spectrum emitted by the sample being imaged may strike the emission filter at angles that are not normal (e.g., orthogonal) to the emission filter, and methods presented herein may be used to correct the raw image data. In some examples, the transmission spectra for the filter at a particular angle of incidence may be generally known, and may be received from the manufacturer of the emission filter. The raw image data may be digitized and received by the computing device from the detector. The raw image data may be used to construct the final image of the sample observable to a user.

Referring now to the preparation stage, steps described herein may be used to gather reference information, and generate correction information, to apply corrections at the correction stage to the raw image data obtained in the measurement stage. For example, step 304B may include receiving information characterizing the emission spectra for a selected reporter. The emission spectra may be over a selected wavelength of the acquired image data. The reporter emission spectra may be based on a received user input indicating a selection of a reporter (step 304A). For example, user may select a reporter emission spectra for commercially available fluorophores, e.g., AF 635. The information characterizing the emission spectra may be generally known. Thus, the information may be retrieved from a library (e.g., database) or from an external source via external network.

Information characterizing the optical performance of the filter may be obtained (step 306A). This information may indicate how the wavelengths of the transmission spectra from the emission filter may shift (e.g., "blueshift," "redshift," etc.) as the angle of incidence changes. The information characterizing the optical performance may be known for the specific filter(s) being used. Thus, the information may be received (e.g., provided by the filter manufacturer), or from a library of data (e.g., database) of optical performance information for filters. In some examples, the information may be determined for the filter analytically. For example, the information may be based on the reporter used, the types of emission and excitation filters used, as well as any other characteristic pertaining to the imaged sample (e.g., field of view, light source, focus, biasing, etc.).

The preparation stage may also include obtaining (e.g., via determining) a reference transmission spectra of the emission filter for a specific angle of incidence (step 306B). The angle of incidence is in respect to the emission filter, and may include both normal angle of incidence (e.g., orthogonal) and oblique (e.g., acute, obtuse) angle of incidence to account for the variation in angle of incidence that has been explained to cause the variation in transmission spectra. Information characterizing the transmission spectra for specific angle of incidence may be known, and may be received from a filter manufacturer or may be determined analytically. In some examples, the one or more processors may utilize a library of data (e.g., a database) comprising of transmission spectra, characteristics pertaining to the image, and associated angles of incidence. In some examples, where the detector generate raw image data based on the transmission spectrum it receives from the emission filter, a computing device may use the detector to retroactively receive the transmission spectrum associated with the raw image data.

Correction information for the selected reporter and emission filter based on angle of incidence may be generated (step 308). This may involve convolving the reporter emission spectrum (step 304B) with the transmission spectra of the emission filter (step 306B). The correction information may be a correction image (e.g., C(x, y)) with correction values to apply to the pixels of the raw image acquired in step 302. The correction values in the correction image, C(c, y), may also be pixels. The pixels may be located in the image by their x and y coordinates (e.g., (x, y)). Generation of the correction information is discussed in further detail below with reference to FIG. 3B.

During the preparation stage, the optical characteristics of the optical imaging system and optical pathway may also be determined. This may include obtaining a reference fluorescence image (e.g., as in step 314), measuring vignetting and read bias (e.g., as in step 312), and obtaining information characterizing optical distortion and determining polynomial correction information (e.g., as in step 310).

At the correction stage, various corrections may be applied to the raw image acquired during the measurement stage in order to obtain a corrected image (step 316). The corrections may be based on the correction information generated during the correction stage. For example, the correction information obtained for the selected reporter and emission filter (step 308) may be applied to the raw image as described above. Other corrections may also be applied based on the information obtained during the preparation stage (steps 310-314), e.g., vignetting, read bias, optical distortion, and the like. For example, vignetting may be corrected by estimating a vignetting function from a reference object, e.g., an empty field, and using the function to normalize the vignetting within the acquired image data. A user may measure, or a computing device may provide measurements for, data (e.g., fluorescence data) on the corrected image (step 318). The corrected image may be presented on a display of a computing device, saved to memory, transmitted via a local and/or wide area network, printed to hardcopy, and the like.

Although some steps in FIG. 3A are being described as being in one of three stages (e.g., steps 304A-314 in a "preparation stage,") the flowchart is not intended to imply any particular order to the steps or the stages. Furthermore, some of the steps identified as being in the preparation stage could be performed after the raw fluorescence image is obtained. As an example, generating correction information (step 310), e.g., by convolving the emission spectra with the transmission spectra could be done anytime, e.g., after the raw fluorescence image is obtained.

Referring now to FIG. 3B, a flowchart 300B of example method steps for generating the correction information (step 308 in FIG. 3A) used to correct for the angles of incidence on an emission filter's field of view is shown. As described above, the correction information may be applied to a raw fluorescence image in order to correct for the spectral shifting of the transmission spectrum provided by the emission filter as a result of those angles of incidence. As described in further detail below, generating the correction information may involve (i) performing a convolution of the emission spectrum for the selected reporter (e.g., a fluorophore) and the transmission spectra of the selected emission filter for each location in the emission filter's field of view, (ii) integrating the result between upper and lower wavelength cutoffs, and (iii) normalizing the result based on the integral of the convolution of the emission spectrum and the transmission spectrum at the reference angle of incidence (e.g., 0°). As described above, generating the correction information may include generating a two-dimensional (2D) pixel-based correction image in which each pixel of the image corresponds to a respective location of the emission filter's field of view and represents a correction to a measured intensity of the transmission spectrum at that location.

As seen in FIG. 3B, information characterizing the emission spectrum for a selected reporter may be obtained (step 322A). The information may be a function of the intensity of the emission spectrum across a wavelength range. That function may be identified as $S(\lambda)$, which gives the intensity of the emission spectrum for a specified wavelength, $\lambda$. As an example, the dashed curve 218 from FIG. 2B depicts a sample emission spectrum for a reporter AF 635. The selected reporter may be a reporter that is used in the imaging of the sample (e.g., a known fluorescent dye).

Additionally, information characterizing transmission spectra for a selected emission filter at multiple angles of incidence may be obtained (step 322B). The information may include, for each angle of incidence, $\theta$, a function of the transmission spectrum across a selected wavelength range for that angle of incidence. This function may be identified as $T(\lambda, \theta)$, which gives the intensity of the transmission spectrum for a specified wavelength, $\lambda$, at the specified angle of incidence, $\theta$. A transmission spectrum may be received for each of the multiple positions of the emission filter's field of view. Each position, (x, y), in the emission filter's field of view corresponds to a particular angle of incidence. Thus, the function that gives the intensity of the transmission spectrum for a position at its corresponding angle of incidence may be identified as $T(\lambda, \theta(x, y))$, where $\theta(x, y)$ is the angle of incidence, $\theta$, resulting from the light ray originating at a position (x, y). As an example, the solid curves 216 from FIG. 2B depict sample transmission spectra for various angles of incidence (e.g., 0°, 5°, 10°, ..., 23°) for a 640/20 nm bandpass filter.

After obtaining information characterizing the emission spectrum for a selected reporter, and obtaining information characterizing the transmission spectra for a selected emission filter at various angles of incidence, correction information may be obtained (steps 324-330) for each position (x, y) in the field of view of the emission filter in order to obtain a correction image C(x, y).

For a position (x, y) at a particular angle of incidence, $\theta$, the intensity of the transmission spectrum may be determined for that position (x, y) and angle of incidence. As each position (x, y) corresponds with a specific angle of incidence at which light strikes the emission filter, an intensity value may be determined using the function of the transmission spectrum across the wavelength range for the specified angle of incidence corresponding with that position.

A convolution may be performed with (i) the function characterizing the emission spectrum, $S(\lambda)$, and (ii) the function characterizing the transmission spectrum for the angle of incidence, $\theta$, corresponding to the position (x, y), $T(\lambda, \theta(x, y))$. The convolution—whose operation is expressed by the symbol "*"—can be identified as: $S(\lambda)*T(\lambda, \theta(x, y))$.

The result of this convolution may be integrated between the upper and lower wavelength cutoff thresholds, $\lambda_{s1}$ and $\lambda_{s2}$, respectively (step 328). The wavelength cutoff thresholds may be the end points of, or may be within the bounds of, the wavelength range at which the emission spectrum for the selected reporter or the transmission spectrum for the selected emission filter is obtained. For example, the wavelength cutoff thresholds may be the end points of the wavelength range of the overlapped region of the emission spectrum for the selected reporter and the transmission spectrum of the selected emission filter. As an example, FIG. 2C depicts exemplary overlapped regions 260a and 260b. For overlapped region 260a, the wavelength range, whose endpoints may be used to form the wavelength cutoff thresholds roughly correspond to 650 nm and 675 nm. Thus, the integrated result may be identified as $\int_{\lambda_{s1}}^{\lambda_{s2}} S(\lambda)*T(\lambda, \theta(x, y))$, where (x, y) is a coordinate position that corresponds to a position in the field of view of the emission filter and, in turn, to a pixel position in the raw image acquired; $S(\lambda)$ is a function characterizing the intensity of the emission spectrum of the reporter; $T(\lambda, \theta(x, y))$ is the function characterizing the intensity of the transmission spectrum from the emission filter for the angle of incidence, $\theta$, that corresponds to the position, (x, y), and $\lambda_{s1}$ and $\lambda_{s2}$ are lower and upper wavelength cutoff thresholds, respectively.

Since the integrated result is based on transmission spectrum affected by variations in the angles of incidence, the integrated result may be "normalized" to quantitatively indicate its relationship to the transmission spectrum of the emission filter at a reference angle of incidence (e.g., the angle of incidence orthogonal to the emission filter's field of view). The normalization may involve dividing the integrated result by a normalization factor. The normalization factor may be an integration of the convolution of the function characterizing the emission spectrum of the reporter, $S(\lambda)$, and a function characterizing the transmission spectrum of the emission filter at a reference angle of incidence, $\theta_0$. The function characterizing the transmission spectrum of the emission filter at the reference angle of incidence can be identified as: $T(\lambda, \theta_0)$. The result of this latter convolution may likewise be integrated between the wavelength cutoff thresholds, $\lambda_{s1}$ and $\lambda_{s2}$. Thus, the result of the integration (step 328) may be normalized with an integration of the result of the convolution of the two functions, $S(\lambda)$ and $T(\lambda, \theta_0)$. It is contemplated that the transmission spectrum at the reference angle of incidence, $\theta_0$, can be the intensity of the transmission spectra at the normal (i.e., 0°) angle of incidence, which will be the center of the field of view of the emission filter. This normalization would provide indications of the respective relationships to the intensities of the transmission spectrum at the respective angles of incidence that deviate from the center of the emission filter's field of view. Thus, an intensity correction may thus be obtained by dividing the result of the first integration involving a particular angle of incidence (step 328) by the normalization factor, e.g., the result of the second integration involving the reference angle of incidence (step 330). As noted above, steps 324 through 330 may be performed for each position (x, y) in the field of view of the emission spectrum.

A correction image, C(x, y) may be obtained by performing the above-described normalization for each position (x, y) of the emission filter's point of view, which correspond to specific angle of incidence (step 332). For purposes of clarity, the correction image C(x, y) may be described as having an "intensity correction" for each position (x, y) of the emission filter's field of view. The raw image acquired (step 302 in FIG. 3A) may thus also be described as having "raw intensities," "original intensities" or "uncorrected intensities" at each position (x, y) of the emission filter's field of view that could be corrected using the "intensity corrections" in the "correction image" to form a corrected image. In one example, the correction image may be an image or image data that includes indicia (e.g., percentages) at each position of the field of view to correct for variations in the transmission spectra resulting from the various angles of incidence.

Thus an intensity correction for a position (x, y) may be a ratio of the integrated convolution of the functions, $S(\lambda)$ and $T(\lambda, \theta(x, y))$ (step 328), with the integrated convolution of the functions, $S(\lambda)$ and $T(\lambda, \theta_0)$ (step 330). Therefore, a correction image C(x, y), may be calculated as follows:

$$C(x, y) = \frac{\int_{\lambda_{S1}}^{\lambda_{S2}} S(\lambda) * T(\lambda, \theta(x, y))}{\int_{\lambda_{S1}}^{\lambda_{S2}} S(\lambda) * T(\lambda, \theta_0)},$$

where (x, y) is a coordinate position that corresponds to a position in the field of view of the emission filter and, in turn, to a pixel position in the raw image acquired; $S(\lambda)$ is a function characterizing the intensity of the emission spectrum of the reporter at a particular wavelength, $\lambda$; $T(\lambda, \theta(x, y))$ is a function characterizing the intensity of the transmission spectrum from the emission filter for the angle of incidence, θ, that corresponds to the position, (x, y), and at the wavelength, λ; $T(\lambda, \theta_0)$ is a function characterizing the intensity of the transmission spectrum from the emission filter at the normal (0°) angle of incidence at the wavelength, λ; and $\lambda_{s1}$ and $\lambda_{s2}$ are lower and upper wavelength cutoff thresholds, respectively.

The equation above may be used to determine an intensity correction for each (x, y) pixel position in the raw image acquired in step 302 in flowchart 300A in FIG. 3A, $I_{ACQUIRED}(x, y)$. Accordingly, there is a one-to-one correspondence between the positions in the correction image, C(x, y), and the pixel positions of the acquired raw image, $I_{ACQUIRED}(x, y)$. The correction image, C(x, y), may thus be used to generate a corrected image, $I_{CORRECTED}(x, y)$.

To obtain the corrected image, $I_{CORRECTED}(x, y)$, a convolution of the acquired raw image, $I_{ACQUIRED}(x, y)$, and the correction image, C(x, y), may be performed—e.g., $I_{corrected}(x, y)=I_{acquired}(x, y)*C(x, y)$, where $I_{acquired}(x, y)$ is the acquired image, "*" indicates a convolution operation, $I_{corrected}(x, y)$ is the corrected image, and C(x, y) is the correction image comprising of intensity corrections for each position, (x, y).

Figure 4A:
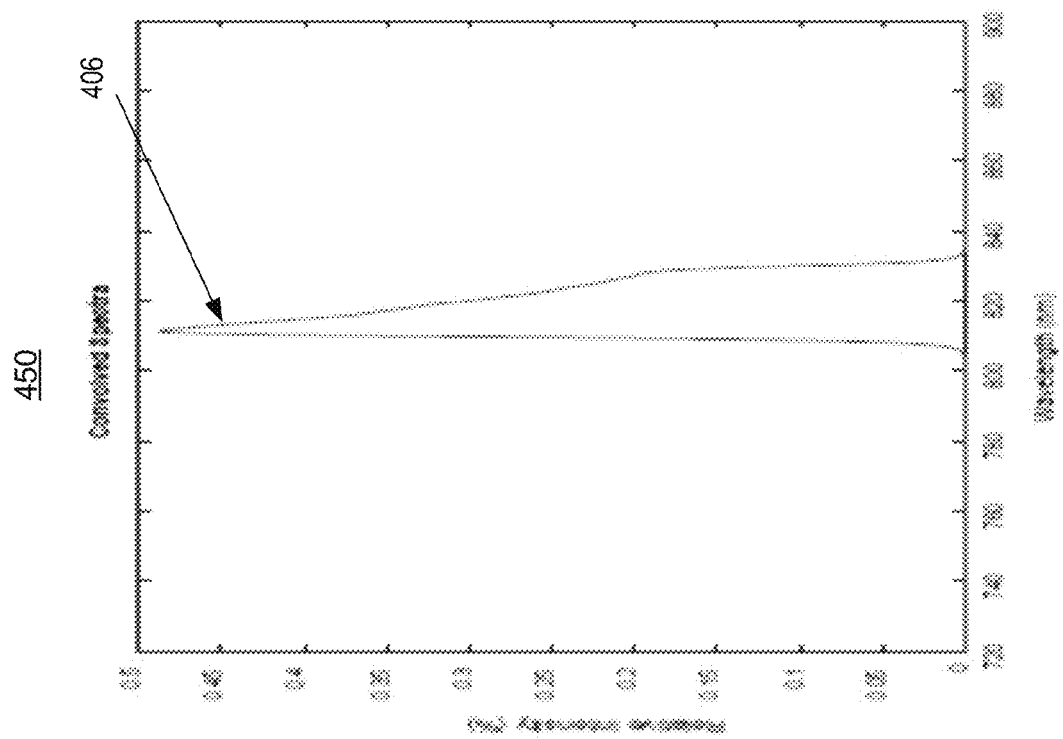
FIG. 4A are graphs depicting the input and output of a convolution operation performed for correcting for the angles of incidence on the field of view of an emission filter.
Figure 4A:
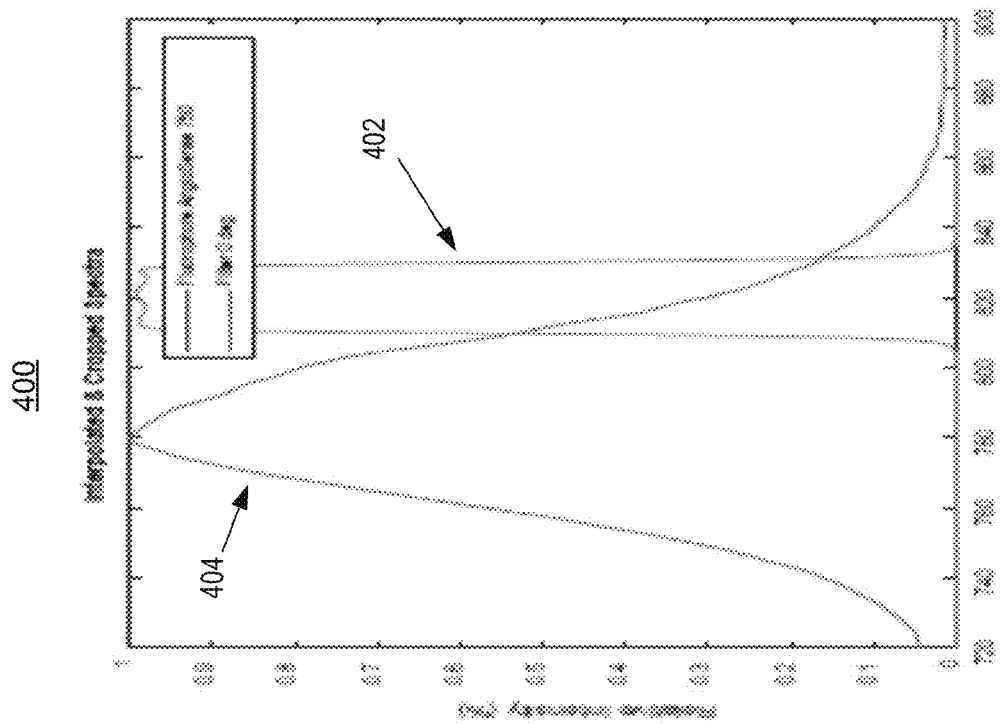

FIG. 4A depicts graphs 400 and 450 illustrating the results of an example convolution operation performed for the emission spectrum of a fluorophore and the transmission spectrum for an emission filter at the normal (0°) angle of incidence. A convolution is a mathematical operation performed on two functions (e.g., a function characterizing a transmission spectrum of an emission filter and a function characterizing an emission spectrum of a reporter) to produce a third function that expresses how the shape of one function is modified by the other function. For example, graph 400 shows an intensity curve 402 of a transmission spectrum of an emission filter and an intensity curve 404 of an emission spectrum of a reporter (e.g., a fluorophore), plotted as a function of their wavelength (e.g., between 720 nm and 900 nm in FIG. 4A). Graph 450 shows a curve 406 representing the convolution of the curve 402 for the transmission spectrum and the curve 404 of the emission spectrum. As seen in graph 450, the wavelength range for the curve 406 resulting from the convolution of the two curves 402 and 404 is from about 805 nanometers to about 830 nanometers, which corresponds with the wavelength range of the overlapping region of the curves 402 and 404 in graph 400. In some implementations, mathematical operations other than convolution (e.g., other numerical implementations of curve multiplication) may be used to express graphs that show how a transmission spectrum of the emission filter may be modified by the emission spectra of the reporter. In addition, methods approximating integration or summation may be alternatively used, when applicable, to perform operations described as integration.

Figure 4B:
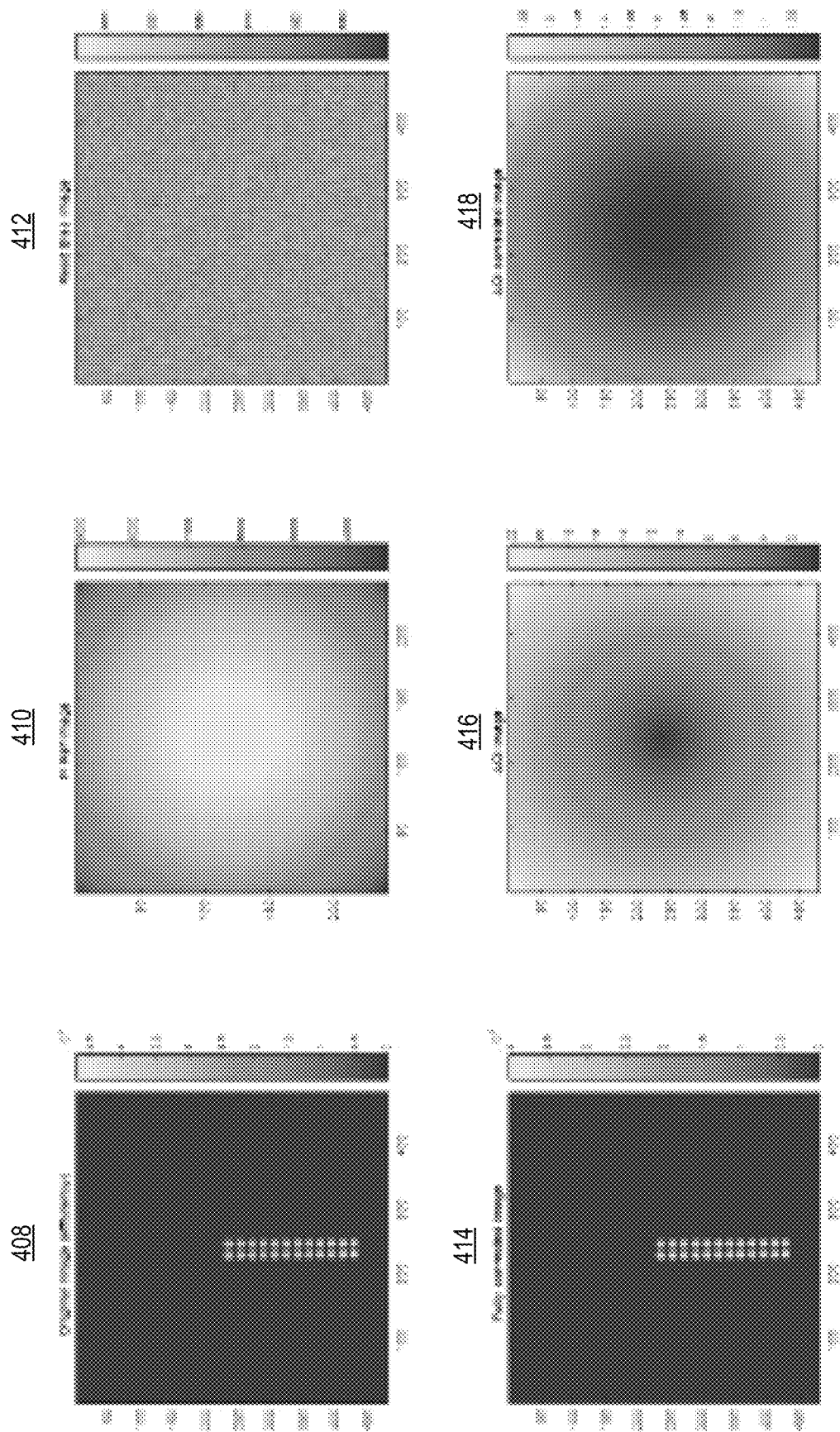
FIG. 4B are sample images that may be used to obtain a corrected fluorescence image.

FIG. 4B depicts a set of example images that may be used to obtain a corrected fluorescence image using the techniques described herein.

The top-left image 408 depicts an example of an acquired raw fluorescence image of a set of wells positioned from the center to the edge of the image. In this example, it is expected that the color of the wells should be uniform. But as shown in image 408, the color of the wells changes from the center to the edge of the acquired raw fluorescence image (e.g., from green at center to yellow at edge). This change in color is due to a change in intensity resulting from the different angles of incidence that deviate from the normal angle of incidence near the edge of the emission filter's field of view.

In contrast, the bottom-left image 414 depicts an example of a corrected image, which has been corrected to account for the spectral shifting observed in the raw fluorescence image 408 due to the different angles of incidence. As seen in image 414, the color has been corrected such that the wells exhibit a more uniform color from the center to the edge of the image as expected. The relative uniformity of the color in image 414, in contrast to the variation in the color in image 408, may be achieved by correcting the intensities of the transmission spectra from the emission filter according to the angle of incidence at which the emission spectrum illuminates the emission filter.

The bottom-middle image 416 depicts another example of an acquired raw fluorescence image. As seen in image 416, the field of view is planar. Each position (x, y) within the field of view corresponds with a specific angle of incidence at which light strikes the emission filter. Thus, a normal (i.e., orthogonal) angle of incidence (e.g., 0°) corresponds to the center of the field of view. As indicated by the shift in color away from the center in image 416, the intensity of the transmission spectrum shifts as angle of incidence changes for off-center positions of the field of view. In other words, as shown by way of example in image 416, there may be a stronger intensity at the center of image 416 where the angle of incidence is orthogonal to the field of view and weaker near edge of image where angle of incidence is more extreme.

The bottom-right image 418 depicts an example of a correction image as described above. Like image 416, the correction image in image 418 is planar, with each position (x, y) corresponding to a position in the raw image 416. The correction image, C(x, y), includes intensity corrections at each position (x, y) to account for the specific angle of incidence corresponding to that position. The intensity corrections across the correction image may vary based on the respective angles of incidence corresponding to the positions (x, y) in the correction image 418.

As previously described above with reference to FIG. 3A, optical characteristics of the optical imaging system and optical pathway may be determined or obtained (e.g., from filter manufacturers). These optical characteristics may also be used to correct the raw image in addition to correcting for variations resulting from the different angles of incidence. The top-middle image 410 and top-right image 412 depict, for example, respectively represent images that may be obtained during the preparation stage. For example, the top middle-image 410 is an example of a reference image, and the top-right image is an example of an image that provides a read bias for the optical imaging system.

Figure 5:
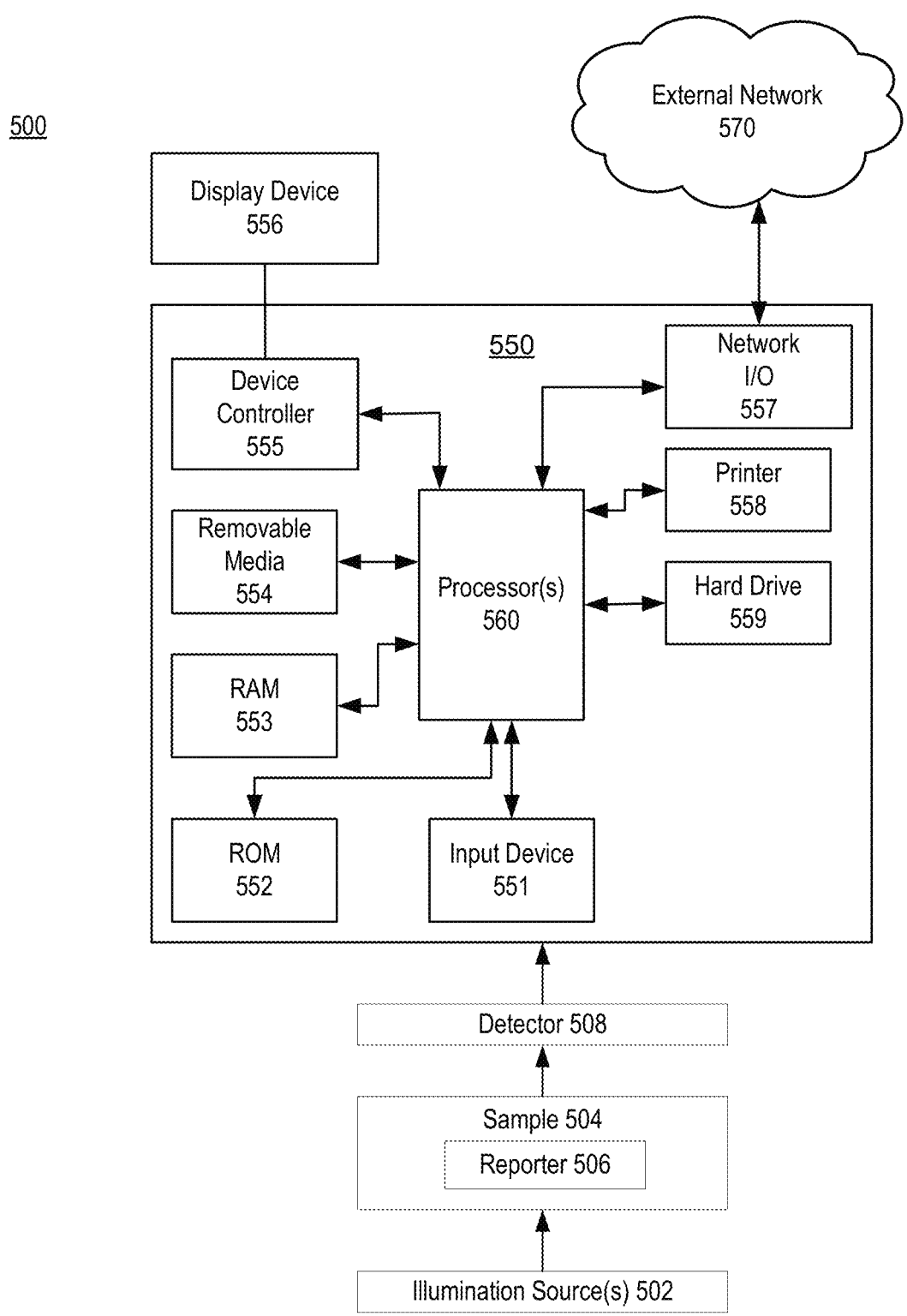
FIG. 5 is a block diagram of example computing hardware on which aspects of the disclosures herein may be implemented.

FIG. 5 illustrates a computing environment 500 that may be used to implement aspects of the disclosure. As described above with reference to FIG. 1, illumination source(s) 502 may illuminate a sample 504, which may excite a reporter 506 (e.g., a fluorophore) causing the sample 504 to emit an emission spectrum that may be filtered and received at a detector 508 (e.g., a CCD). The detector 508 may provide a signal corresponding to the detected spectrum to the input device 551 of the computing device 550.

Systems of the disclosure may include a computing device 550 which executes software that controls the operation of one or more instruments, and/or that processes data obtained by the system. The software may include one or more modules recorded on machine-readable media such as magnetic disks, magnetic tape, CD-ROM, and semiconductor memory, for example. The machine-readable medium may be resident within the computer or can be connected to the computer by a network I/O 557 (e.g., access via external network 570). However, in alternative examples, one can substitute computer instructions in the form of hardwired logic for software, or one can substitute firmware (i.e., computer instructions recorded on devices such as PROMS, EPROMS, EEPROMs, or the like) for software. The term machine-readable instructions as used herein is intended to encompass software, hardwired logic, firmware, object code and the like.

The computing device 550 may be programmed with specific instructions to perform the various image processing operations described herein. The computer can be, for example, a specially-programmed embedded computer, a personal computer such as a laptop or desktop computer, or another type of computer, that is capable of running the software, issuing suitable control commands, and/or recording information in real-time. The computer may include a display 556 for reporting information to an operator of the instrument (e.g., displaying a raw fluorescence image, a correction image, a corrected image, etc.), an input device 551 (e.g., keyboard, mouse, interface with optical imaging system, etc.) for enabling the operator to enter information and commands, and/or a printer 556 for providing a printout, or permanent record, of measurements made by the system and for printing images. Some commands entered at the keyboard may enable a user to perform certain data processing tasks. In some implementation, data acquisition and data processing are automated and require little or no user input after initializing the system.

The computing device 550 may comprise one or more processors 560, which may execute instructions of a computer program to perform any of the functions described herein. The instructions may be stored in a read-only memory (ROM) 552, random access memory (RAM) 553, removable media 554 (e.g., a USB drive, a compact disk (CD), a digital versatile disk (DVD)), and/or in any other type of computer-readable medium or memory (collectively referred to as "electronic storage medium"). Instructions may also be stored in an attached (or internal) hard drive 555 or other types of storage media. The computing device 550 may comprise one or more output devices, such as a display device 556 (e.g., to view generated images) and a printer 558, and may comprise one or more output device controllers 555, such as an image processor for performing operations described herein. One or more user input devices 551 may comprise a remote control, a keyboard, a mouse, a touch screen (which may be integrated with the display device 556), etc. The computing device 550 may also comprise one or more network interfaces, such as a network input/output (I/O) interface 557 (e.g., a network card) to communicate with an external network 570. The network I/O interface 557 may be a wired interface (e.g., electrical, RF (via coax), optical (via fiber)), a wireless interface, or a combination of the two. The network I/O interface 557 may comprise a modem configured to communicate via the external network 570. The external network may comprise, for example, local area network, a network provider's wireless, coaxial, fiber, or hybrid fiber/coaxial distribution system (e.g., a DOCSIS network), or any other desired network.

One or more of the elements of the computing device 550 may be implemented as software or a combination of hardware and software. Modifications may be made to add, remove, combine, divide, etc. components of the computing device 550. Additionally, the elements shown in FIG. 5 may be implemented using computing devices and components that have been specially configured and programmed to perform operations such as are described herein. For example, a memory of the computing device 550 may store computer-executable instructions that, when executed by the processor 560 and/or one or more other processors of the computing device 550, cause the computing device 550 to perform one, some, or all of the operations described herein. Such memory and processor(s) may also or alternatively be implemented through one or more Integrated Circuits (ICs). An IC may be, for example, a microprocessor that accesses programming instructions or other data stored in a ROM and/or hardwired into the IC. For example, an IC may comprise an Application Specific Integrated Circuit (ASIC) having gates and/or other logic dedicated to the calculations and other operations described herein. An IC may perform some operations based on execution of programming instructions read from ROM or RAM, with other operations hardwired into gates or other logic. Further, an IC may be configured to output image data to a display buffer.

Thus, systems and methods described herein can be used to generate more accurate images (e.g., fluorescence images), by correcting for variations in the measured intensity of the transmission spectra from emission filters due to different angles of incidence. More accurate imaging may have tremendous benefits, which can help a user to analyze more accurate in vivo images, identify and characterize areas of disease to distinguish diseased and normal tissue, such as detecting tumor margins that are difficult to detect, etc. Furthermore, accurate images would be particularly useful in high throughput imaging, involving multiple live subjects.

While the disclosures have been particularly shown and described with reference to example implementations, it should be understood by those skilled in the art that various changes in form and detail may be made therein without departing from the spirit and scope of claimed subject matter.

What is claimed is:

1. A method of generating an image comprising:
   receiving, from an emission filter, a transmission spectrum corresponding to a selected wavelength range of an emission spectrum, wherein the emission spectrum illuminates the emission filter at a plurality of angles of incidence that deviate from a normal angle of incidence with respect to the emission filter;
   measuring an intensity of the transmission spectrum;
   obtaining a convolution function by performing, for one or more positions of a field of view of the emission filter, a convolution of (i) a function characterizing a known emission spectrum of a reporter, and (ii) a function characterizing a known transmission spectrum for an angle of incidence corresponding to a position of the one or more positions;
   obtaining, based on the convolution function and based on a spectral response of the emission filter as a function of the plurality of angles of incidence, a corrected intensity for the transmission spectrum; and
   generating, based on the transmission spectrum and the corrected intensity, an image.

2. The method of claim 1, wherein the emission spectrum is emitted from a luminescent source in a sample, the luminescent source comprising one of:
   a fluorescent source,
   a bioluminescent source,
   a phosphorescent source, and
   a chemiluminescent source.

3. The method of claim 2, wherein the sample is biological.

4. The method of claim 1 wherein obtaining the corrected intensity further comprises:
obtaining an integrated convolution function by integrating the convolution function between a lower wavelength threshold and an upper wavelength threshold.

5. The method of claim 4 wherein obtaining the corrected intensity further comprises:
normalizing the integrated convolution function based on an intensity of a known transmission spectrum for the emission filter at a reference angle of incidence.

6. The method of claim 5 wherein the reference angle of incidence is an angle of incidence that is normal to the emission filter.

7. The method of claim 5, wherein the normalizing comprises:
obtaining a reference convolution function by performing a convolution of the function characterizing the known emission spectrum and a function characterizing the known transmission spectrum for the emission filter at the reference angle of incidence;
obtaining an integrated reference convolution function by integrating the reference convolution function between the lower wavelength threshold and the upper wavelength threshold; and
dividing the integrated convolution function by the integrated reference convolution function.

8. The method of claim 1, wherein obtaining a corrected intensity comprises:
generating a correction image comprising, for one or more positions of a field of view of the emission filter, a correction to an intensity of the transmission spectrum measured at a position of the one or more positions.

9. The method of claim 8, wherein generating the image comprises:
acquiring a raw image comprising, for one or more positions of a field of view of the emission filter, a measured raw intensity of the transmission spectrum; and
performing a convolution of the raw image and the correction image.

10. A system for fluorescence imaging, comprising:
a light source that provides excitation spectrum;
an excitation filter that provides, toward a sample, a selected excitation wavelength range from the excitation spectrum;
an emission filter that provides a transmission spectrum comprising a selected emission wavelength range of an emission spectrum received from the sample, wherein the emission filter receives the emission spectrum at a plurality of angles of incidence that deviate from a normal angle of incidence with respect to the emission filter;
a fluorescence detector that measures intensity of the transmission spectrum across a field of view of the emission filter; and
a computing device storing instructions that, when executed by one or more processors of the computing device, corrects the intensity based on spectral shifting of the transmission spectrum as a function of the plurality of angles of incidence.

11. The system of claim 10, further comprising collimating optics positioned between the sample and the emission filter.

12. The system of claim 10, wherein:
the instructions, when executed, generate a digital image comprising a plurality of pixels;
each pixel corresponds to a respective position of a plurality of positions of the field of view of the emission filter;
each pixel comprises a value corresponding to the intensity of the transmission spectrum measured at the respective position of the field of view of the emission filter; and
each respective position corresponds to an angle of incidence of the plurality of angles of incidence.

13. The system of claim 12, wherein the instructions, when executed, corrects the intensity by modifying, for a pixel of the plurality of pixels, the value corresponding to the intensity of the transmission spectrum based on the angle of incidence of the respective position of the field of view of the emission filter that corresponds to the pixel.

14. The system of claim 13, wherein:
the instructions, when executed, modify the pixel by applying a correction to the pixel; and
the instructions, when executed, obtain the correction to apply to the pixel by:
obtaining a convolution function by performing, for the plurality of positions of the field of view of the emission filter, a convolution of (i) a function characterizing a known emission spectrum of a reporter, and (ii) a function characterizing a known transmission spectrum for an angle of incidence of the plurality of angles of incidence that corresponds to a position of the plurality of positions;
obtaining a reference convolution function by performing a convolution of (i) the function characterizing a known emission spectrum of a reporter, and (ii) a function characterizing a function characterizing the transmission spectrum at an angle of incidence that is normal to the emission filter;
obtaining an integrated convolution function and an integrated reference convolution function by respectively integrating the convolution function and the reference convolution function between a lower wavelength threshold and an upper wavelength threshold; and
dividing the integrated convolution function by the integrated reference convolution function.

15. The system of claim 14, wherein the instructions, when executed:
generate a correction image comprising the correction to apply to the pixel; and
apply the correction to the pixel by performing a convolution of the digital image and the correction image.

16. A method for generating a fluorescence image, the method comprising:
acquiring fluorescence image data comprising a plurality of pixels, wherein each pixel corresponds to a respective intensity of a transmission spectrum measured at a position of a field of view of an emission filter illuminated by an emission spectrum, and wherein the emission spectrum illuminates the field of view at a plurality of angles of incidence;
based on a known emission spectrum of a fluorophore and based on spectral shifting of the transmission spectrum as a function of the plurality of angles of incidence, generating a correction image comprising a plurality of correction values;
applying the plurality of correction values to the fluorescence image data to obtain a plurality of corrected pixels, wherein each corrected pixel corresponds to a respective corrected intensity of the transmission spectrum; and generating the fluorescence image using the plurality of corrected pixels.

17. The method of claim 16, further comprising receiving user input indicating a selection of the fluorophore and indicating a selection of the emission filter.

18. The method of claim 16, wherein the plurality of correction values is based on a ratio of:
   (a) an first integration of a convolution of (i) a function characterizing a known emission spectrum of the fluorophore and (ii) a function characterizing a known transmission spectrum for an angle of incidence corresponding to a position of the field of view of the emission filter, to
   (b) an second integration of a convolution of (i) the function characterizing the known emission spectrum of the fluorophore, and (ii) a function characterizing a known transmission spectrum for the emission filter at a normal angle of incidence.

19. The method of claim 18, wherein the first integration and the second integration are integrated between a lower wavelength threshold and an upper wavelength threshold.

\* \* \* \* \*